(12) United States Patent
Hvichia et al.

(10) Patent No.: US 6,783,928 B2
(45) Date of Patent: Aug. 31, 2004

(54) MICROSTRUCTURES FOR CELL PROLIFERATION ASSAYS AND SEMEN ANALYSIS

(76) Inventors: Georgi Hvichia, 10640 Lockart Rd., Philadelpia, PA (US) 19116; Paolo Gasparini, Via Castel Gonnelle, 8-25030 Brandico (IT)

( * ) Notice: Subject to any disclaimer, the term of this patent is extended or adjusted under 35 U.S.C. 154(b) by 281 days.

(21) Appl. No.: 09/907,896

(22) Filed: Jul. 17, 2001

(65) Prior Publication Data

US 2003/0017525 A1 Jan. 23, 2003

(51) Int. Cl.⁷ .................................................. A01N 1/02
(52) U.S. Cl. ........................... 435/2; 435/2; 435/305.4; 435/395; 422/58; 436/63
(58) Field of Search ........................ 435/2, 395, 305.4; 422/58; 436/63

(56) References Cited

U.S. PATENT DOCUMENTS

| | | |
|---|---|---|
| 4,176,953 A | 12/1979 | Bartoov et al. |
| 5,427,946 A | 6/1995 | Kricka et al. |
| 5,486,335 A | 1/1996 | Wilding et al. |
| 5,744,366 A * | 4/1998 | Kricka et al. |
| 5,866,345 A | 2/1999 | Wilding et al. |
| 5,928,880 A | 7/1999 | Wilding et al. |
| 5,942,443 A * | 8/1999 | Parce et al. |
| 6,091,502 A * | 7/2000 | Weigl et al. |

OTHER PUBLICATIONS

Kricka et al., "Sperm testing with microfabricated glass-capped silicon microchannels," Clin. Chem. 40(9):1823 (1994).

Kricka et al., "Applications of a microfabricated device for evaluated sperm function," Clin. Chem. 39:1944 (1993) Abstract only.

* cited by examiner

Primary Examiner—Leon B. Lankford, Jr.
(74) Attorney, Agent, or Firm—Akin Gump Strauss Hauer & Feld, L.L.P.

(57) ABSTRACT

The invention relates to microscale cell handling apparatus which exhibit bulk fluid flow properties superior to prior art microscale cell handling devices. The microscale cell handling apparatus described herein comprises at least two flow paths, each of which extend between an inlet region and an outlet region of a void that can be filled with fluid. The apparatus includes a microscale flow path (i.e., a flow path having a cross-sectional area of about 1 to 1000 square micrometers at its narrowest point) and a non-microscale flow path (i.e., a flow path having a cross-sectional area greater than 1000 square micrometers at its narrowest point). The apparatus can have multiple microscale and non-microscale flow paths. The void can be enclosed within a cover.

60 Claims, 6 Drawing Sheets

MICROSTRUCTURES FOR CELL PROLIFERATION ASSAYS AND SEMEN ANALYSIS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Developments in methods of manufacturing very small devices, such as microelectronic devices, have made it possible to precisely and reproducibly make devices having features with nanometer-scale dimensions. Apart from use of such methods in microelectronic device production, similar technology has been used to make devices for handling biological materials, such as cells and macromolecules.

Microengineered bio-handling devices having structural elements with minimal dimensions ranging from tens of micrometers (the dimensions of biological cells) to nanometers (the dimensions of some biological macromolecules) have been described. This range of dimensions (nanometers to tens of micrometers) is referred to herein as "microscale." For example, U.S. Pat. No. 5,928,880, U.S. Pat. No. 5,866, 345, U.S. Pat. No. 5,744,366, U.S. Pat. No. 5,486,335, and U.S. Pat. No. 5,427,946 describe microscale devices for handling cells and biological molecules.

About half of infertility cases are attributable to sperm motility dysfunction. Diagnosing such dysfunction can be difficult. Prior art methods of assessing sperm motility include manual observation and counting of sperm using a gradated device such as a Makler chamber, a microscope, and a hand-held push-button counter. In addition to being time— and labor—intensive, such methods are susceptible to operator-to-operator differences in operation. There is a need for sperm motility-assessing devices that are simpler to operate manually, or which can be automated.

Hemocytometry is a field of medical analysis and research wherein blood cells are analyzed using variety of techniques and devices. Basic manually-operated devices such as microscope slides with Neubauer or Makler chambers were developed over a century ago. These devices are expensive, reusable, and lack flexibility, multiple features, and disposability. Disposability is especially desirable to minimize medical personnel interaction with potentially hazardous biological specimens.

Knowledge of rates of growth and proliferation of cells (e.g., mammalian cells, yeast, fungi, and cells infected with viruses) is critical for many research and clinical applications. However, there are few, if any, analytical devices which can be used for objective measurement of growth and proliferation of cells under certain conditions, such as conditions which simulate dimensions and complexity of tissues, organs, and extracellular matrices.

A significant shortcoming of previously described microscale cell— and biomolecule—handling devices is that bulk fluid flow and other fluid dynamic phenomena through microscale channels and spaces often interferes with measurements which the devices are intended to enable. The origin of such phenomena cannot always be determined or controlled, and can be attributable to temperature, mechanical pressure, hydrodynamic pressure, and surface tension forces, for example. Microscale biohandling devices would be significantly improved if this shortcoming could be overcome.

The invention described in this disclosure overcomes this shortcoming.

BRIEF SUMMARY OF THE INVENTION

The invention relates to an apparatus for analyzing cells. The apparatus comprises a base and at least two obstacles. The base defines a void for containing a liquid medium. The void has an inlet region, an outlet region, and a differentiating region interposed between the inlet and outlet regions. The obstacles are disposed within the void and define a microscale flow path and a non-microscale flow path between the inlet and outlet regions. Preferably, the cross-sectional area of the narrowest portion of the non-microscale flow path is at least 10, 100, or 1000 times the cross-sectional area of the narrowest portion of the microscale flow path. The apparatus can comprise enough obstacles to define a plurality of microscale and non-microscale flow paths, and these can vary in size. For example, one microscale flow path can be 2, 5, or 10 or more times wider than another. Alternatively, the microscale flow paths can all have about the same width. The obstacles can, for example, be elongate members (e.g., walls) that define a microscale flow path having an approximately constant width.

The distance between the base and the more distal surface of the obstacles can be approximately constant along the length of the microscale flow path defined by the elongate members. Alternatively, this distance can vary (continuously, semi-continuously, or in a stepwise fashion) along the length of the microscale flow path.

The precise construction of the obstacles is not critical. They can, for example, be connected to the base (or cover) at one or several points, or along the entire length of the obstacles. They can be connected by projections extending from one of the base (or cover) and the obstacles. In another embodiment, the obstacles are integral with the base (or cover).

The apparatus can be used with or without a cover that covers at least a portion of the void. When the apparatus has a cover, the obstacles can be connected to either or both of the cover and the base. Also, when a cover is used, at least one of the base and the cover is transparent. The cover or base can have gradations marked, imprinted, engraved, or otherwise associated therewith along a microscale flow path. The cover can have one or mole holes or ports therein for providing fluid to and withdrawing fluid from the apparatus, and those holes or ports can be adapted to fit or receive a fluid handling device (pump, tube, pipe, pippettor, etc.).

In another aspect, the invention relates to an apparatus for assessing the motility of cells in a sample. This apparatus comprises a unitary body having a surface with depressed portions. The depressed portions define a) an inlet region for receiving the sample;
b) an outlet region for containing a fluid medium;
c) a microscale channel fluidly connecting the inlet and outlet regions, for facilitating movement of cells between the inlet and outlet regions; and
d) a non-microscale channel fluidly connecting the inlet and outlet regions for facilitating bulk fluid movement.

The surface can further define e) a substantially flat upper surface bordering each of the microscale and non-microscale channels.

This surface can be used for receiving a substantially flat cover opposed against the upper surface. Alternatively, the surface can further define e) a plurality of projections extending from each of the microscale and non-microscale channels.

Those projections can be used for receiving a substantially flat cover opposed against the projections. The features of this apparatus can otherwise be like the corresponding features of the apparatus described above.

The invention includes a method of assessing cell motility in a sample containing cells. The method comprises applying the sample to the inlet region of an apparatus described herein. Movement of cells from the inlet region to the outlet region by way of the microscale flow path is assessed in order to assess the cells' motility. In this method, convective flow of the fluid medium in the void is preferably equilibrated or halted prior to applying the sample to the inlet region. This method is useful, for example, for assesing motility of human, equine, bovine, sheep, goat, canine, and feline spermatozoa.

The invention also includes a method of separating more motile cells from less motile cells in a sample. The method comprises applying the sample to the inlet region of an apparatus described herein. More motile cells are more likely than less motile cells to move from the inlet region to the outlet region. More motile cells are collected from the outlet region.

In yet another aspect, the invention includes a method of assessing proliferation of cells in a sample. This method comprises applying the sample to the inlet region of an apparatus described herein. Cells in the inlet region can proliferate and give rise to cells which are generated along the microscale flow path. The presence of cells along the microscale flow path is assessed in order to assess proliferation of the cells.

The invention further relates to a method of assessing motile cells in a sample obtained from the blood of an animal. This method comprises applying the sample to the inlet region of an apparatus described herein. Motile cells in the sample move along the microscale flow path. The presence of cells is assessed along the microscale flow path as an indication of the presence of motile cells in the sample.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

FIG. 1 comprises FIGS. 1A–1G.

FIG. 2 comprises FIGS. 2A–2I.

DETAILED DESCRIPTION OF THE INVENTION

Figure 1A:
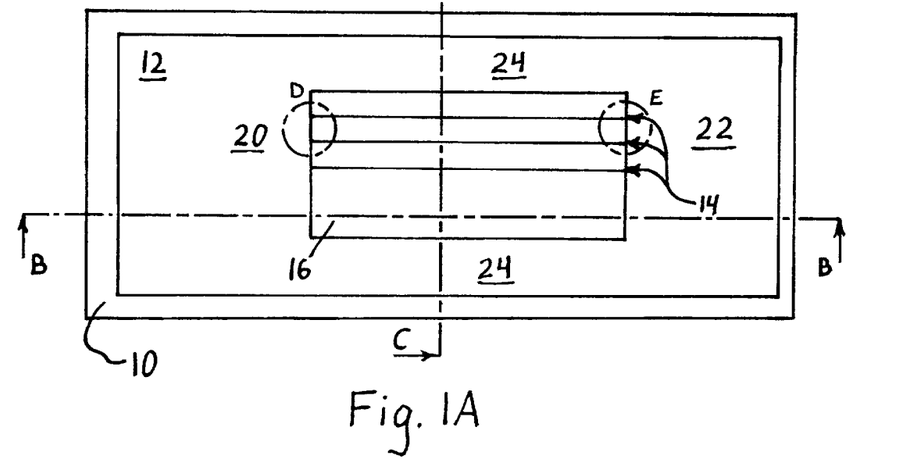
FIG. 1A is an overhead view of a microscale cell handling apparatus described herein.
Figure 1B:
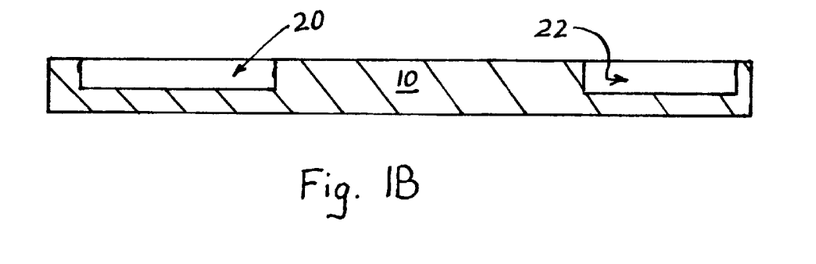
FIGS. 1B and 1C are side views of the apparatus shown in FIG. 1A.
Figure 1C:
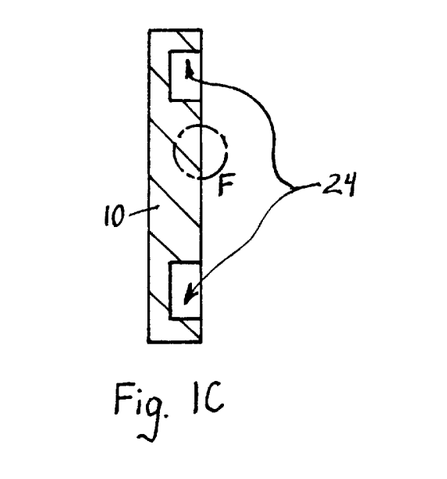
Figure 1D:
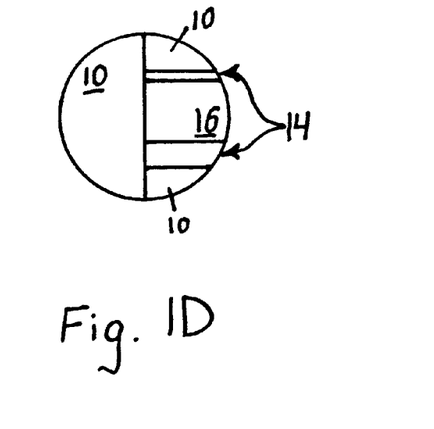
FIG. 1D is a detail of the inlet region of the apparatus.
Figure 1E:
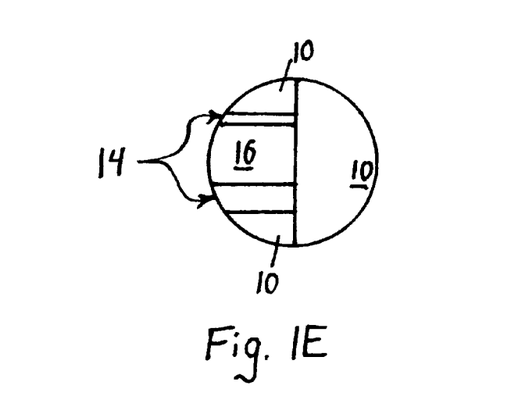
FIG. 1E is a detail of the outlet region of the apparatus.
Figure 1F:
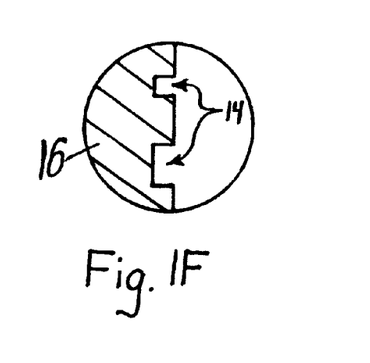
FIG. 1F is a detail of the side view shown in FIG. 1C.
Figure 1G:
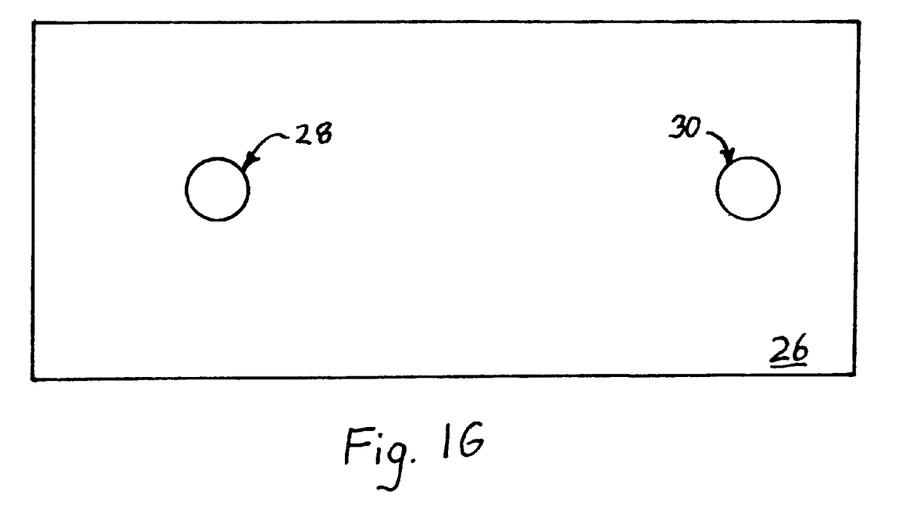
FIG. 1G is an overhead view of a cover adapted for the apparatus shown in FIG. 1A.
Figure 2A:
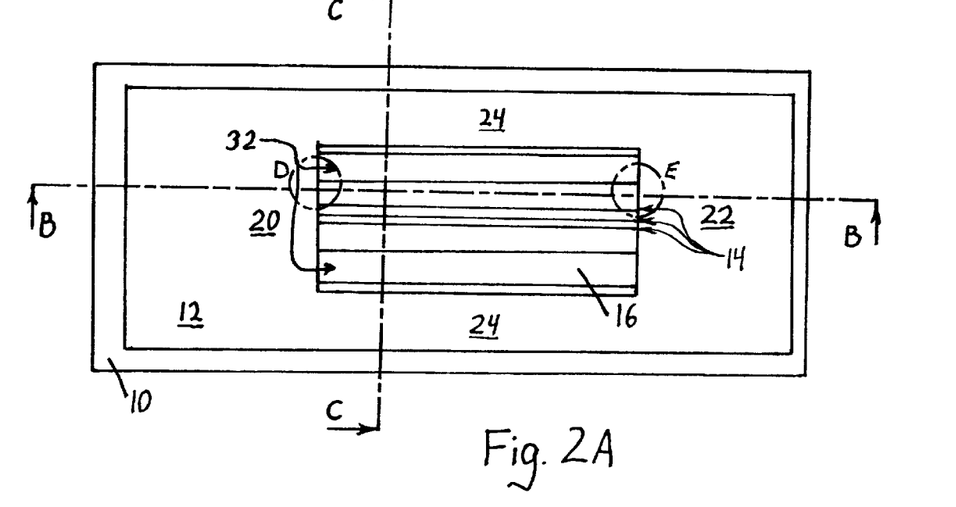
FIG. 2A is an overhead view of a microscale cell handling apparatus described herein.
Figure 2B:
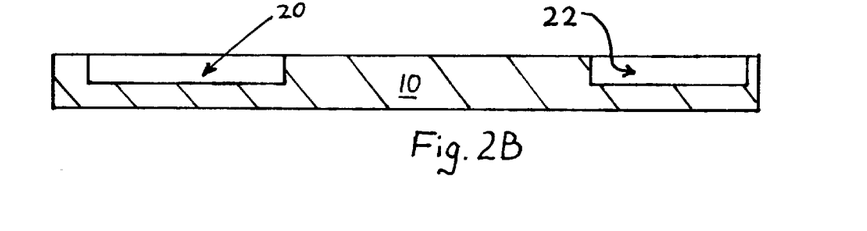
FIGS. 2B and 2C are side views of the apparatus shown in FIG. 2A.
Figure 2C:
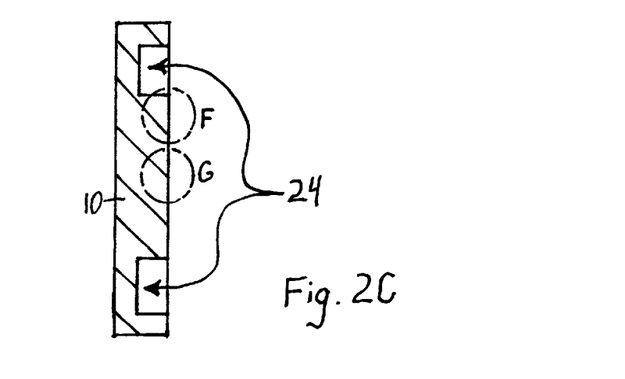
Figure 2D:
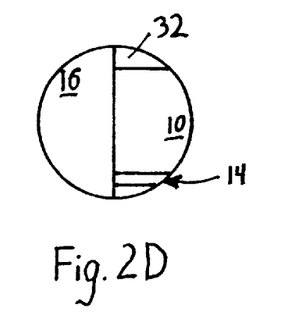
FIG. 2D is a detail of the inlet region of the apparatus.
Figure 2E:
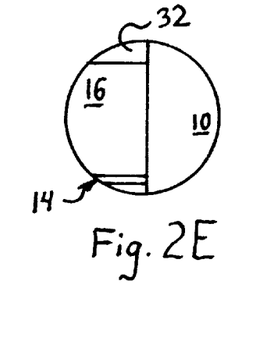
FIG. 2E is a detail of the outlet region of the apparatus.
Figure 2F:
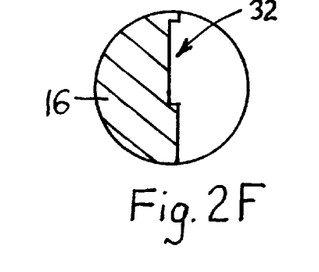
FIGS. 2F and 2G are details of the side view shown in FIG. 2C.
Figure 2G:
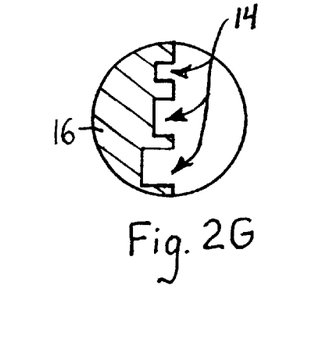
Figure 2H:
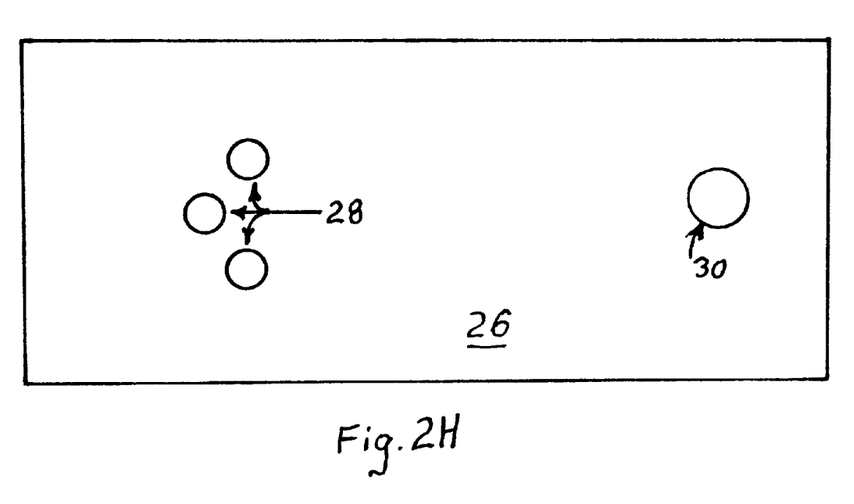
FIG. 2H is an overhead view of a cover adapted for the apparatus shown in FIG. 2A.

The invention relates to microscale cell handling apparatus which exhibit fluid dynamic properties (e.g., bulk fluid flow properties) superior to prior art microscale cell handling devices. The microscale cell handling apparatus described herein comprises at least two flow paths, each of which extends between an inlet region (20, element numbers referring to those used in the figures) and an outlet region (22) of a void (12) that can be filled with fluid. One flow path is a microscale flow path (i.e., a flow path having a cross-sectional area of about 1 to 1000 square micrometers at its narrowest point; elements 14 in the figures). The other flow path is a non-microscale flow path (i.e., a flow path having a cross-sectional area greater than 1000 square micrometers at its narrowest point; elements 24 in the figures).

The non-microscale fluid path has much larger cross-sectional area at its narrowest point than the microscale fluid path. For example, the non-microscale fluid path can have an area 10, 25, 50, 100, 250, 500, or 1000 times or more greater than the microscale fluid path. In one embodiment, the non-microscale flow path can be likened to a 'pool' (or large void) that is in fluid communication with both ends of the microscale flow path. Bulk fluid flow through the non-microscale flow path permits equilibration of fluid forces between the inlet and outlet regions of the void in which the microscale and non-microscale fluid paths are situated. Without being bound by any particular theory of operation, the inventors believe that bulk fluid flow through the microscale fluid path is limited, and there is significantly less interference with cell behavior in the microscale fluid path than occurs in prior art microscale cell handling devices.

The lower limit for the desirable cross-sectional area of the microscale flow path depends on the type of cells to be examined using the device and the characteristics of those cells. For example, devices which are to be used to analyze human sperm cells should have microscale flow paths that have a cross-sectional area large enough to accommodate movement of sperm cells therethrough. Human sperm cells have a diameter of about 2 to 4 micrometers, measured perpendicularly to the long axis of the cell. Thus, microscale flow channels for accommodating movement of human sperm therethrough should have a minimum dimension not less than 2–4 micrometers. For example, such microscale flow paths can have the form square troughs having a height of about 2 to 4 micrometers, a depth of 2–4 micrometers, and substantially any length (e.g., tens, hundreds, thousands, or tens of thousands of micrometers in length). As a result, such flow paths can have cross-sectional areas of as little as 4–16 square micrometers. Of course, flow paths having greater cross-sectional area (e.g., 25, 50, or 100 square micrometers) can also be used for sperm analysis. Further by way of example, human blood platelets can be about 1 to 3 micrometers in diameters, human red blood cells can be about 6.5 to 8 micrometers in diameter, and human leukocytes can be 5 to 15 micrometers in diameter, depending on their type. Depending on the desired use of the apparatus, the cross-sectional area of the microscale flow path is preferably selected so that cells are able to move past one another, so that the flow path will not become obstructed by a single slow-moving cell.

The apparatus described herein can be used to more accurately assess characteristics of cells which can be affected or obscured by convective fluid flow. For example, certain types of cells (e.g., spermatozoa, some blood cells, and certain types of bacteria) exhibit intrinsic motility. In still fluid, these cells can move on their own, at least under certain circumstances. However, forces exerted on the cell by bulk movement of the fluid in which it is suspended can be orders of magnitude greater than the force generated by the cell's intrinsic motility. Thus, when the fluid in which the cells are suspended is flowing, it can be difficult to detect how much, if any, motility the cells exhibits. Bulk fluid flow frequently occurs in prior art microscale cell handling devices, but can be minimized or substantially eliminated using the apparatus described herein.

The apparatus described herein has a relatively large fluid channel (i.e., a non-microscale flow path; 24) in addition to the microscale flow path (14). Pressure imbalance is the force that drives fluid flow. A pressure difference between an inlet region (20) and outlet region (22) of a fluid-filled void (12) will drive flow of fluid from the region of higher pressure to the region of lower pressure. A narrow fluid path exerts greater resistance to fluid flow than a larger fluid path. Hence, if the inlet and outlet regions are connected by both a first fluid path having a large cross-sectional area at its narrowest point and a second fluid path having a smaller cross-sectional area, a greater proportion of fluid flow will occur through the first path. If the area of the first path is one or more orders of magnitude greater than the area of the second path and the pressure difference between the inlet and outlet regions is not extreme, fluid flow through the second path can be minimal. The apparatus described herein takes advantage of this property of fluid systems to minimize bulk fluid flow through the microscale flow path.

The apparatus comprises a base (10) which defines a void (12) for containing a liquid medium (e.g., water, saline, phosphate-buffered saline, natural or artificial human fallopian tubal fluid, cervical mucus, or some other solution or suspension in which cells can be suspended or induced to grow or multiply). The void has an inlet region (20) to which cells can be provided and an outlet region (22). Interposed between the inlet and outlet regions is a differentiating region in which at least two obstacles (16) are disposed. The obstacles define a microscale flow path (14). The microscale flow path has a cross sectional area of about 1 to 1000 square micrometers at its narrowest point. Thus, fluid flow from the inlet region to the outlet region through the microscale flow path passes between at least two of the obstacles. In some embodiments, very wide microscale flow paths (32) can be used, in which the width of the microscale flow path is much greater than the depth of the microscale flow paths. Such very wide microscale flow paths can be useful for observing cells in the apparatus.

The inlet and outlet regions are also connected by a non-microscale flow path. The non-microscale flow path has a cross sectional area at least about ten times greater thatn the cross-sectional area of the microscale flow path, e.g. greater than about 1000 square micrometers at its narrowest point when the apparatus has a microscale flow path with a square cross section of 10 micrometers on a side. The apparatus can comprise multiple microscale flow paths, multiple non-microscale flow paths, or both.

The microscale flow path can have a depth (i.e., the distance between the top and bottom portions of the flow path, relative to gravity, in a closed flow path, or from the fluid surface to the bottom portion of the flow path in an open flow path) that varies over the length (i.e., from inlet to outlet regions) of the flow path. The depth can vary gradually (i.e., in the form of a sloped bottom portion) or step-wise over the length of the flow path. Certain cells (e.g., spermatozoa and certain bacteria) are believed to exhibit a preference for one or more particular positions in a fluid column, and the apparatus having a microscale flow path of varying depth can be used to assess this phenomenon.

The spacing between flow paths is preferably at least a few cell diameters, in order to minimize movement of cells from one flow path to an adjacent one. For example, flow paths can be separated by at least about 10 micrometers, and preferably by 50–1000 micrometers.

When the apparatus is filled with fluid, the fluid fills the void and the flow paths. If desired, the apparatus can be lightly manipulated (e.g., by tapping or shaking), or the fluid can be applied under pressure, in order to ensure that all flow paths are filled with the fluid and to remove any air bubbles that may be present. Air bubbles, if present, can also be removed by passing fluid from the inlet region to the outlet region. The void and flow paths need not necessarily be completely filled. It is sufficient that a layer of fluid at least 1–10 micrometers deep (i.e., sufficiently deep to accommodate a cell of the type to be analyzed, and preferably at least a few cell diameters deep) is present in the microscale flow path. In a preferred embodiment, the flow paths are closed so that they can be completely filled with fluid. Completely filled flow paths do not have an air-fluid interface, and surface tension forces attributable to interaction of cells with an air-fluid interface can therefore be minimized.

The obstacles are situated in the void of the body between the inlet and outlet regions. The precise means by which the obstacles are kept in the void is not critical. The can, for example, be connected to either the base or the cover, or they can be one or more separate pieces of material disposed in the boid between the base and the cover. In a preferred embodiment, the obstacles and the base are a unitary piece of material. For example, the obstacles and the surfaces defining the void in the base can be formed by removing (e.g., by machining or etching) portions of the base. The obstacles define a microscale flow path by being closely situated near one another (e.g., 10 nanometers to 50 micrometers apart, preferably 5 to 25 micrometers apart). In one embodiment, the obstacles are simply 'posts' or cylindrical or oval-cylindrical extensions of the base into the void. In a preferred embodiment, the obstacles have the form of elongate members (i.e., walls) that define a channel. Such a channel can have a square, rectangular, semi-circular, semi-oval or other cross-sectional profile, or it can be a groove (e.g., a 'V' shaped groove) in the base. The portion of the obstacle furthest from the base can be flattened (i.e., to accept a substantially flat cover), or it can have one or more protrusions extending therefrom (i.e., to support a cover). In other embodiments, the obstacles are adhered to the base, compressed against the base, or otherwise held in place. The obstacles can be part of an insert that is placed into the void, or they can be extensions of a cover which is applied to the void, as described herein. In the latter embodiment, the obstacles need not be connected with the body if the device is to be inverted such that fluid is held by gravity on the cover and within the microscale flow path.

The apparatus can comprise a cover (26) which closes at least the microscale flow path (i.e., by being connected to the obstacles defining the microscale flow path along their entire length), or it can comprise a cover which rests upon protrusions extending from the obstacles, the base, or both. In the latter embodiment, there can be a gap between the cover and the obstacles, along at least part of their length. This gap can facilitate filling of the microscale flow path with fluid, owing to surface tension forces between the cover and the non-contacting edge of the obstacles, which forces can draw fluid into the flow path. In a preferred embodiment, the cover has an area that is greater than the void in the base, and completely encloses the void (i.e., including both the microscale flow path and some or all of the non-microscale flow path) when the cover is applied to the base. The base, cover, and obstacles can be precisely machined so that when the base and cover are joined, the obstacles are connected to both the cover and the base. For instance, the obstacles can be integral with one of the cover and the base and compressed against the other of the cover and the base. Alternatively, the obstacles can be fused with both the cover and the base, or there can be a very small gap between the obstacles and at least one of the cover and the base. This gap is preferably less than the width of a cell of the type to be analyzed using the apparatus (e.g., less than about 1 micrometer if red blood cells are to be analyzed, or less than about 2 micrometers if sperm are to be analyzed). There can also be a large gap between the cover and the obstacles (or between the obstacles and the surface of the void, if the obstacles are connected to or rest upon the cover and the apparatus is to be used with the cover on the bottom of the apparatus), so that there is a space above the fluid medium in the flow paths and the ceiling of the apparatus (i.e., between the obstacles and the cover if the apparatus is used with the cover on top or between the obstacles and a portion of the surface of the void if the apparatus is used with the cover on the bottom).

The cover, base, and obstacles (if not already connected to one of the cover and base) can be provided in the form of a kit to be assembled by the user (e.g., after adding a fluid medium to the void in the base).

When the apparatus does not comprise a cover (i.e., when the flow paths are not closed), it is preferable that the apparatus is used in a humidified environment (e.g., at 90–100% relative humidity). Humidification methods and apparatus are known in the art, and can be performed on a facility-wide-, single room-, or enclosed space-basis, ore even on an enclosed microscope stage.

The flow paths (or at least the microscale flow paths) can be treated with any of a variety of known reagents (e.g., oxygen plasma) in order to increase the hydrophilicity of the surfaces of the flow path. This treatment can improve the rate and completeness of filling of the flow paths with a fluid medium introduced into the apparatus. Furthermore, if there are surfaces of the apparatus (e.g., the upper surface of one or more obstacles in an apparatus in which there is a space above the obstacles that is not filled with fluid medium during operation) that are not intended to be in contact with the fluid medium of the apparatus during its operation, then those surfaces can be treated with any of a variety of known reagents (e.g., various silylating reagents) in order to increase the hydrophobicity of the surfaces.

The cover, the base, or both, can have one or more fluid access ports (28 and 30), whereby fluid can be added to or withdrawn from the void when the device is assembled. In one embodiment, the cover has a fluid inlet port (28) in fluid communication with the inlet region (20) of the void (12) when the cover (26) and base (10) are assembled. In another embodiment the cover instead (or also) has a port (30) in fluid communication with the outlet region (22) of the void (12) when the cover (26) and base (10) are assembled. The ports can be simple holes which extend through the cover, or they can have fixtures (burrs, rings, hubs, or other fittings) associated with them for facilitating connection of a fluid handling device with the port. These ports facilitate addition and withdrawal of fluid and allow application of cells to the apparatus or collection of cells therefrom.

The base, cover, and obstacles can be constructed from substantially any material that will hold its shape during operation of the apparatus as described herein. However, rigid materials are preferred. Examples of suitable materials include various glasses, solid polymers, and crystalline minerals. Silicon is a preferred substrate material because of the well-developed technology permitting its precise and efficient fabrication, but other materials can be used, including various glasses and cast, molded, or machined polymers including polytetrafluoroethylenes. The inlet and outlet ports, the obstacles, and the surfaces defining the void in the base can be fabricated inexpensively in large quantities from a silicon substrate by any of a variety of micromachining methods known to those skilled in the art. The micromachining methods available include film deposition processes such as spin coating and chemical vapor deposition, laser fabrication or photolithographic techniques such as UV or X-ray processes, or etching methods which may be performed by either wet chemical processes or plasma processes. (See, e.g., Manz et al., Trends in Analytical Chemistry, 10: 144–149 (1991)).

Flow paths of varying widths and depths can be fabricated with microscale dimensions for use in analyzing a sample containing cells. A silicon substrate containing a fabricated microscale flow path can be covered and sealed (e.g., anodically bonded) with a thin glass cover. Other clear or opaque cover materials may be used. Alternatively, two silicon substrates can be sandwiched, or a silicon substrate can be sandwiched between two glass covers. Preferably, at least one of the base and the cover is transparent. Use of a transparent material facilitates dynamic viewing of the contents of the device, and allows optical probing of the microscale flow system either visually or by machine. Other fabrication approaches can be used.

The apparatus can be chemically treated or coated with any of a variety of known materials which reduce or enhance agglutination of cells with the material selected for the cover, base, or obstacles.

The apparatus can have indicia associated in a fixed position with respect to the microscale flow path. The indicia can be used to assess the position of a cell in the microscale flow path, and can thus be used to determine motility or flow rates of a cell in the path. The indicia can be printed, painted, or stamped on, or engraved or etched in the base or the cover, preferably on a surface of a component that is transparent, so that the indicia and the cells in the microscale flow path can be simultaneously observed by a user. The indicia preferably do not alter the shape, diameter, or smoothness of the flow path with which they are associated. For example, the indicia can be on or in the opposite face of a transparent material in which the flow path exists. Alternatively, the indicia can be on or in one face of a transparent material that has a different face opposed against the flow path (e.g., the exterior face of the cover).

The apparatus is used by filling the void with enough fluid that the microscale flow path contains the fluid at a depth equal to at least the minimum dimension of the cells to be analyzed using the device (e.g., at least 1 micrometer deep if blood platelet cells are to be analyzed, or at least 2–4 micrometers deep if sperm are to be analyzed). If the apparatus has a cover, then the microscale flow path is preferably completely filled with fluid for a selected period of time (e.g., seconds, minutes, or hours). After adding fluid to the void, fluid levels within the device are permitted to equilibrate. Equilibration of fluid levels can be speeded by gently shaking, rocking, or tapping the device. After equilibration, there should be at least one microscale flow path and one non-microscale fluid path that are not obstructed by air bubbles. The fluid in the void is preferably equilibrated such that there is no fluid flow in the microscale and non-microscale flow paths prior to further use of the device. Alternatively, a steady flow of fluid through the device can be established (e.g., by connecting the inlet and outlet regions of the void to a fluid handling device such as a pump). For example, electrolytic or electroosmotic fluid flow can be induced in the microscale flow path in the direction from the outlet toward the inlet in order to provide resistance to cell movement (of course, the flow can be induced in the direction from the inlet region toward the outlet region, if desired).

The apparatus can be supplied pre-filled with fluid. In one embodiment, the fluid does not fill the region between the upper surface of the obstacles and the ceiling of the void (i.e., between the obstacles and the cover if the apparatus is used with the cover on top or between the obstacles and a portion of the surface of the void if the apparatus is used with the cover on the bottom). In this embodiment, the fluid level can be lower than the upper surface of the obstacles (i.e., the flow paths are filled below at a level below the upper surface of the obstacles), at approximately the same level as the upper surface of the obstacles, or slightly above the upper surface of the obstacles. In this third instance, surface tension forces can permit the fluid medium to bulge above the upper surface of the obstacles without flowing across the upper surface (i.e., so that there is no fluid path between flow channels across the upper surfaces of the obstacles). The ability of the fluid to bulge above the upper surface of the obstacles without flowing between flow channels can be enhanced by increasing the spacing between the flow paths, by treating the upper surfaces of the obstacles with a hydrophobicity-enhancing agent, or both.

Cells are introduced into the void at the inlet region. If the cells move from the spot at which they are introduced (i.e., by growth, proliferation, or motility), then the cells can enter the microscale flow path. The presence of cells in the microscale flow path is an indication that the cells have moved there from the inlet region. Cells can move through the entire length (e.g., 10 nanometers to hundreds, thousands, or tens of thousands of micrometers) of the microscale flow path to the outlet region of the void. There, the cells can be observed, enumerated, or collected. If it is considered important to separate cells which have arrived at the outlet region by way of the microscale flow path from cells which arrived there by way of the non-microscale flow path, then the non-microscale flow path is preferably much longer (measured from inlet to outlet) than the microscale flow path.

The apparatus can be used to assess motility of cells in a sample. The apparatus is assembled as described herein (i.e., including the fluid medium), any fluid flow is equilibrated, and then the sample is delivered to the inlet region of the void. Any motile cells in the sample move from the inlet region, and some will (by chance) enter a microscale flow path of the apparatus. The apparatus preferably has a plurality of microscale flow paths of varying minimum cross-sectional areas. Over time, motile cells will probabilistically move farther from the inlet region, and those in the microscale flow path can move toward the outlet region. By assessing the number of cells in the microscale flow path, the distribution of cells along the microscale flow path, the farthest distance from the inlet region of a cell in the microscale flow path, the time needed for a cell to reach a particular location in the microscale flow path, or some combination of these, the motility of cells in the sample can be assessed. Samples which contain relatively few motile cells or cells which have less motility will result in fewer cells in the microscale flow path or cells which are not as far advanced along the microscale flow path toward the outlet region than samples which contain relatively more motile cells or cells which have greater motility.

The ability of the apparatus to differentiate between rapidly motile cells (i.e., cells which exhibit relatively high motility) and less rapidly motile (or non-motile) cells enables one to separate these cells using the device. A sample containing cells believed (or known) to exhibit different degrees of motility is applied to the inlet region of the void. Cells which exhibit greater motility will move away from the inlet region more rapidly than cells which exhibit lesser motility. Some of the more rapidly motile cells will enter a microscale flow path and proceed thence toward the outlet region. Less rapidly motile cells will generally enter the microscale flow path(s) later than the more rapidly motile cells, and will progress more slowly along the microscale flow path. Hence, cells exit the microscale flow path (i.e., either at the outlet region of the void or at an intermediate chamber fluidly connected with both the inlet and outlet regions by way of microscale flow paths) at times that roughly correspond with the degree of motility they exhibit. At later times, the cells that emerge from the microscale flow path will be a mixture of cells which exhibit relatively high motility and relatively low motility. Non-motile cells will pass through the microscale flow path at a much slower rate. If isolation of less rapidly motile cells is desired, then multiple iterations of this procedure can be performed, rapidly motile cells and substantially non-motile cells being collected and discarded during each iteration, and only cells which exit the microscale flow path at intermediate times used in the next iteration.

Preparative-scale devices can have a multiplicity of microsclae flow paths extending radially (e.g., in one plane or in multiple planes) from an inner region to an outer region. At least one non-microscale flow path also connectects the inner and outer regions. Either region can be used as an inlet for a sample containing cells, and the other region can be used as an outlet to collect cells which move through the microscale flow paths. Preferably, the length of the non-microscale flow path(s) are much longer than the length (s) of th emicroscale flow paths (e.g., the non-microscale flow path is curved, spiral, or tortuous).

The apparatus described herein can also be used to assess the relative rate of growth or proliferation of cells in a sample. In this method, the sample is applied to the inlet region of the assembled, fluid-filled apparatus. The fluid with which the apparatus is filled is preferably a growth-supporting medium, such as any of the known media which contain nutrients and minerals capable of supporting cell growth and proliferation. The apparatus is maintained under conditions which encourage growth or proliferation of cells in the sample. Growth or proliferation is assessed by observing the presence or absence of cells within a microscale flow path of the apparatus. The extent of growth along the microscale flow path (i.e., measured from the inlet region in the direction of the outlet region of the void) can indicate the extent of growth or proliferation of cells in the sample. Furthermore, if the apparatus comprises a plurality of microscale flow paths which communicate with the inlet region at different geometric locations, then the presence or absence of cells in various microscale flow paths (e.g., paths which communicate with the inlet region at a point farthest from the location at which the sample is applied) can indicate the degree of cell growth or proliferation as well.

The closely-spaced nature of the obstacles that define the microscale flow path can simulate physiological growth habitats more nearly than simple open-plate cell culture methods, and can facilitate easier observation of cells which might otherwise optimally be cultured in a difficult-to-image three-dimensional matrix. For example, bone and cartilage cells can be cultured in three-dimensional matrices, and non-destructive observation of those cells in those matrices can be difficult to achieve. If the depth of the fluid in the microscale flow path varies, then the presence or absence of cells at various levels (i.e., depths) of the flow path can indicate important characteristics of the cells, such as the propensity of the cells to flourish at certain hydrodynamic pressures.

It will be appreciated by those skilled in the art that changes could be made to the embodiments described above without departing from the broad inventive concept thereof. It is understood, therefore, that this invention is not limited to the particular embodiments disclosed, but covers modifications within the spirit and scope of the present invention as defined by the appended claims.

What is claimed is:

1. An apparatus for analyzing cells, the apparatus comprising
   a) a base defining a void for containing a liquid medium, the void having an inlet region, an outlet region, and a differentiating region interposed between the inlet and outlet regions; and
   b) at least two obstacles disposed within the void, the obstacles defining
      i) a microscale flow path between the inlet and outlet regions in the differentiating region of the void and
      ii) a non-microscale flow path between the inlet and outlet regions.

2. The apparatus of claim 1, wherein the cross-sectional area of the narrowest portion of the non-microscale flow path is at least 10 times the cross-sectional area of the narrowest portion of the microscale flow path.

3. The apparatus of claim 1, wherein the cross-sectional area of the narrowest portion of the non-microscale flow path is at least 100 times the cross-sectional area of the narrowest portion of the microscale flow path.

4. The apparatus of claim 1, wherein the cross-sectional area of the narrowest portion of the non-microscale flow path is at least 1000 times the cross-sectional area of the narrowest portion of the microscale flow path.

5. The apparatus of claim 1, wherein the obstacles define a plurality of microscale flow paths.

6. The apparatus of claim 5, wherein the plurality of microscale flow paths includes a microscale flow path having a narrowest portion at least 2 times greater than the narrowest portion of another microscale flow path.

7. The apparatus of claim 5, wherein the plurality of microscale flow paths includes a microscale flow path having a narrowest portion at least 5 times greater than the narrowest portion of another microscale flow path.

8. The apparatus of claim 5, wherein the plurality of microscale flow paths includes two microscale flow paths having narrowest portions that are substantially equal in cross-sectional area.

9. The apparatus of claim 1, wherein the obstacles are elongate members that define a microscale flow path having an approximately constant width.

10. The apparatus of claim 9, wherein the distance between the base and the more distal surface of the obstacles is approximately constant along the length of the microscale flow path defined by the elongate members.

11. The apparatus of claim 9, wherein the distance between the base and the more distal surface of the obstacles varies along the length of the microscale flow path defined by the elongate members.

12. The apparatus of claim 11, wherein the distance between the base and the more distal surface of the obstacles varies step-wise along the length of the microscale flow path defined by the elongate members.

13. The apparatus of claim 9, wherein the elongate members define a plurality of non-microscale flow paths.

14. The apparatus of claim 1, wherein the obstacles are connected to the base.

15. The apparatus of claim 1, wherein the base and the obstacles are connected along the entire length of the obstacles.

16. The apparatus of claim 1, wherein the base and obstacles are connected by projections extending from one of the base and the obstacles.

17. The apparatus of claim 1, wherein the obstacles are integral with the base.

18. The apparatus of claim 1, further comprising
   c) a cover covering at least a portion of the void.

19. The apparatus of claim 18, wherein the obstacles are connected to the cover.

20. The apparatus of claim 18, wherein the obstacles are integral with the cover.

21. The apparatus of claim 18, wherein the obstacles are elongate members that define a microscale flow path having an approximately constant width.

22. The apparatus of claim 21, wherein the distance between the cover and the more distal surface of the obstacles is approximately constant along the length of the microscale flow path defined by the elongate members.

23. The apparatus of claim 21, wherein the distance between the cover and the more distal surface of the obstacles varies along the length of the microscale flow path defined by the elongate members.

24. The apparatus of claim 23, wherein the distance between the cover and the more distal surface of the obstacles varies step-wise along the length of the microscale flow path defined by the elongate members.

25. The apparatus of claim 18, wherein at least one of the base and the cover is transparent.

26. The apparatus of claim 25, wherein both the base and the cover are transparent.

27. The apparatus of claim 25, wherein the obstacles are elongate members and wherein at least one of the base and the cover bears gradations along the microscale flow path.

28. The apparatus of claim 18, wherein the cover covers substantially the entire void in the base.

29. The apparatus of claim 28, wherein the cover has a first hole extending therethrough in fluid communication with the inlet region of the void.

30. The apparatus of claim 29, further comprising an adapter for aligning a fluid handling device with the first hole.

31. The apparatus of claim 30, wherein the adapter is integral with the cover.

32. The apparatus of claim 29, wherein the cover has a second hole extending therethrough in fluid communication with the outlet region of the void.

33. The apparatus of claim 32, further comprising an adapter for aligning a fluid handling device with the second hole.

34. The apparatus of claim 33, wherein the adapter is integral with the cover.

35. The apparatus of claim 18, wherein the base, the obstacles, and the cover are unitarily bonded.

36. The apparatus of claim 18, wherein the base and the obstacles are connected by compression.

37. The apparatus of claim 18, wherein the cover and the obstacles are connected by compression.

38. The apparatus of claim 37, wherein the base and the obstacles are connected by compression.

39. The apparatus of claim 18, wherein the cover and the obstacles are connected along the entire length of the obstacles.

40. The apparatus of claim 18, wherein the cover and the obstacles are connected by projections extending from one of the cover and the obstacles.

41. The apparatus of claim 18, wherein at least one of the base and the cover comprises a unitary piece of a material selected from the group consisting of a glass, a solid polymer, and a crystalline mineral.

42. The apparatus of claim 41, wherein at least one of the base and the cover comprises a unitary piece of silicon.

43. The apparatus of claim 41, wherein the material is treated with a reagent known to reduce cell agglutination with the material.

44. The apparatus of claim 41, wherein the material is treated with a reagent known to increase cell agglutination with the material.

45. A apparatus for assessing the motility of cells in a sample, the apparatus comprising a unitary body having a surface with depressed portions that define
   a) an inlet region for receiving the sample;
   b) an outlet region for containing a fluid medium;
   c) a microscale channel fluidly connecting the inlet and outlet regions, for facilitating movement of cells between the inlet and outlet regions; and
   d) a non-microscale channel fluidly connecting the inlet and outlet regions for facilitating bulk fluid movement.

46. The apparatus of claim 45, wherein the surface further defines
   e) a substantially flat upper surface bordering each of the microscale and non-microscale channels, for receiving a substantially flat cover opposed against the upper surface.

47. The apparatus of claim 46, further comprising the cover opposed against the upper surface.

48. The apparatus of claim 45, wherein the surface further defines
   e) a plurality of projections extending from each of the microscale and non-microscale channels, for receiving a substantially flat cover opposed against the projections.

49. The apparatus of claim 48, further comprising the cover opposed against the projections.

50. The apparatus of claim 45, wherein the cross-sectional area of the narrowest portion of the non-microscale channel is at least 10 times the cross-sectional area of the narrowest portion of the microscale channel.

51. The apparatus of claim 45, wherein the cross-sectional area of the narrowest portion of the non-microscale channel is at least 100 times the cross-sectional area of the narrowest portion of the microscale channel.

52. The apparatus of claim 45, wherein the cross-sectional area of the narrowest portion of the non-microscale channel is at least 1000 times the cross-sectional area of the narrowest portion of the microscale channel.

53. A method of assessing cell motility in a sample containing cells, the method comprising
   1) applying the sample to the inlet region of an apparatus comprising
      a) a base defining a void which contains a liquid medium, the void having the inlet region, an outlet region, and a differentiating region interposed between the inlet and outlet regions;
      b) at least two obstacles connected to the base, the obstacles defining
         i) a microscale flow path between the inlet and outlet regions in the differentiating region of the void and
         ii) a non-microscale flow path between the inlet and outlet regions; and
      c) a cover connected to the obstacles; and
   2) assessing movement of cells from the inlet region to the outlet region by way of the microscale flow path.

54. The method of claim 53, wherein convective flow of the fluid medium in the void is equilibrated prior to applying the sample to the inlet region.

55. The method of claim 53, wherein convective flow of the fluid medium in the void is halted prior to applying the sample to the inlet region.

56. The method of claim 53, wherein the cells are spermatozoa.

57. The method of claim 56, wherein the spermatozoa are selected from the group consisting of human, equine, bovine, sheep, goat, canine, and feline spermatozoa.

58. A method of separating more motile cells from less motile cells in a sample, the method comprising
   1) applying the sample to the inlet region of an apparatus comprising
      a) a base defining a void which contains a liquid medium, the void having the inlet region, an outlet region, and a differentiating region interposed between the inlet and outlet regions;
      b) at least two obstacles connected to the base, the obstacles defining
         i) a microscale flow path between the inlet and outlet regions in the differentiating region of the void and
         ii) a non-microscale flow path between the inlet and outlet regions, wherein the volume of the non-microscale flow path is at least 10 times the volume of the microscale flow path; and
      c) a cover connected to the obstacles, whereby more motile cells are more likely than less motile cells to move from the inlet region to the outlet region; and
   2) collecting more motile cells from the outlet region.

59. A method of assessing proliferation of cells in a sample, the method comprising
   1) applying the sample to the inlet region of an apparatus comprising
      a) a base defining a void which contains a liquid medium, the void having the inlet region, an outlet region, and a differentiating region interposed between the inlet and outlet regions;
      b) at least two obstacles connected to the base, the obstacles defining
         i) a microscale flow path between the inlet and outlet regions in the differentiating region of the void and
         ii) a non-microscale flow path between the inlet and outlet regions; and
      c) a cover connected to the obstacles, whereby cells in the inlet region can proliferate and give rise to cells which are generated along the microscale flow path; and 2) assessing the presence of cells along the microscale flow path.

60. A method of assessing motile cells in a sample obtained from the blood of an animal, the method comprising
1) applying the sample to the inlet region of an apparatus comprising
   a) a base defining a void which contains a liquid medium, the void having the inlet region, an outlet region, and a differentiating region interposed between the inlet and outlet regions;
   b) at least two obstacles connected to the base, the obstacles defining
      i) a microscale flow path between the inlet and outlet regions in the differentiating region of the void and
      ii) a non-microscale flow path between the inlet and outlet regions; and
   c) a cover connected to the obstacles, whereby motile cells in the sample move along the microscale flow path; and
2) assessing the presence of cells along the microscale flow path.

* * * * *